United States Patent
Santra et al.

(10) Patent No.: US 9,676,741 B1
(45) Date of Patent: Jun. 13, 2017

(54) CO-CRYSTAL OF DAPAGLIFLOZIN WITH CITRIC ACID

(71) Applicant: Sun Pharmaceutical Industries Limited, Munbai, Maharashtra (ID)

(72) Inventors: Ramkinkar Santra, Paschim Medinipur (IN); Tarun Kumar Singh, Lucknow (IN); Ram Thaimattam, Hyderabad (IN); Mohan Prasad, Gurgaon (IN)

(73) Assignee: SUN PHARMACEUTICAL INDUSTRIES LIMITED, Mumbai (IN)

( * ) Notice: Subject to any disclaimer, the term of this patent is extended or adjusted under 35 U.S.C. 154(b) by 0 days.

(21) Appl. No.: 15/321,007

(22) PCT Filed: Jun. 23, 2015

(86) PCT No.: PCT/IB2015/054709
§ 371 (c)(1),
(2) Date: Dec. 21, 2016

(87) PCT Pub. No.: WO2015/198227
PCT Pub. Date: Dec. 30, 2015

(30) Foreign Application Priority Data

Jun. 23, 2014 (IN) .......................... 1670/DEL/2014

(51) Int. Cl.
*A61K 31/70* (2006.01)
*C07H 15/04* (2006.01)
*C07D 309/10* (2006.01)
*C07C 59/265* (2006.01)

(52) U.S. Cl.
CPC .......... *C07D 309/10* (2013.01); *C07C 59/265* (2013.01); *C07B 2200/13* (2013.01)

(58) Field of Classification Search
CPC ............................ A61K 31/7004; C07H 15/08
USPC ............................................ 514/23; 536/120
See application file for complete search history.

(56) References Cited

U.S. PATENT DOCUMENTS

| | | |
|---|---|---|
| 6,515,117 B2 | 2/2003 | Ellsworth et al. ............ 536/17.2 |
| 6,774,112 B2 | 8/2004 | Gougoutas ....................... 514/23 |
| 7,375,213 B2 | 5/2008 | Deshpande et al. .......... 536/124 |
| 7,919,598 B2 | 4/2011 | Gougoutas et al. ......... 536/1.11 |
| 7,932,379 B2 | 4/2011 | Deshpande et al. .......... 536/124 |
| 2013/0303467 A1 | 11/2013 | Gougoutas et al. ............ 514/23 |

FOREIGN PATENT DOCUMENTS

| | | | |
|---|---|---|---|
| WO | WO 2012/154812 | 11/2012 | ........... C07D 409/10 |
| WO | WO 2012/163546 | 12/2012 | ......... A61K 31/7004 |
| WO | WO 2013/079501 | 6/2013 | ........... C07D 309/10 |
| WO | WO 2014/178040 | 11/2014 | ............... C07H 7/04 |

OTHER PUBLICATIONS

International Search Report and Written Opinion for International Application No. PCT/IB2015/054709, issued by PCT on Oct. 17, 2015.
International Preliminary Report on Patentability for International Application No. PCT/IB2015/054709, issued by PCT on Jan. 5, 2017.

*Primary Examiner* — Raymond Henley, III

(57) ABSTRACT

The present invention relates to a dapagliflozin-citric acid co-crystal, processes for its preparation, and its use for the treatment of type 2 diabetes mellitus. A dapagliflozin citric acid co-crystal. The dapagliflozin citric acid co-crystal of claim 1, characterized by X-ray powder diffraction peaks having d-spacing values at about 3.89, 3.90, 4.01, 4.35, 5.77, and 5.80.

9 Claims, 3 Drawing Sheets

CO-CRYSTAL OF DAPAGLIFLOZIN WITH CITRIC ACID

FIELD OF THE INVENTION

The present invention relates to a dapagliflozin-citric acid co-crystal, processes for its preparation, and its use for the treatment of type 2 diabetes mellitus.

BACKGROUND OF THE INVENTION

Dapagliflozin propanediol monohydrate of Formula I, the marketed form of dapagliflozin, is chemically described as D-glucitol, 1,5-anhydro-1-C-[4-chloro-3-[(4-ethoxyphenyl) methyl]phenyl]-, (1S)-, compounded with (2S)-1,2-propanediol, hydrate (1:1:1). It is indicated as an adjunct to diet and exercise to improve glycemic control in adults with type 2 diabetes mellitus.

Formula I

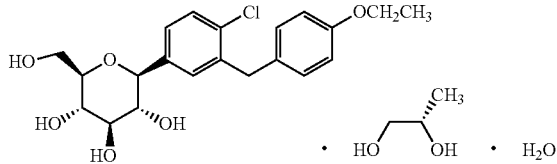

U.S. Pat. No. 6,774,112 discloses crystalline complexes of C-aryl glucosides with natural amino acids like (L)-phenylalanine and (L)-proline.

U.S. Pat. No. 7,919,598 discloses crystalline complexes of dapagliflozin with propylene glycol, ethanol, ethylene glycol, L-proline, and L-phenylalanine, and processes for their preparation.

PCT Publication No. WO 2012/163546 discloses inclusion complexes of dapagliflozin and cyclodextrin, and processes for their preparation.

PCT Publication No. WO 2013/079501 discloses crystalline dapagliflozin hydrate and processes for its preparation.

PCT Publication No. WO 2014/178040 discloses dapagliflozin lactose co-crystals and dapagliflozin asparagine co-crystals.

In the pharmaceutical industry, there is a constant need to identify the critical physicochemical parameters such as novel salts, polymorphic forms, and co-crystals that affect the drug's performance, stability, etc., which may play a key role in determining a drug's market acceptance and success.

The discovery of new forms of a pharmaceutical product can provide materials having desirable processing properties, such as ease of handling, storage stability, and ease of purification. Accordingly, the present inventors have found a novel co-crystal form of dapagliflozin having enhanced storage stability, solubility, and processability.

SUMMARY OF THE INVENTION

The present invention provides a dapagliflozin-citric acid co-crystal, processes for its preparation, and its use for the treatment of type 2 diabetes mellitus.

DETAILED DESCRIPTION OF THE INVENTION

Figure 1:
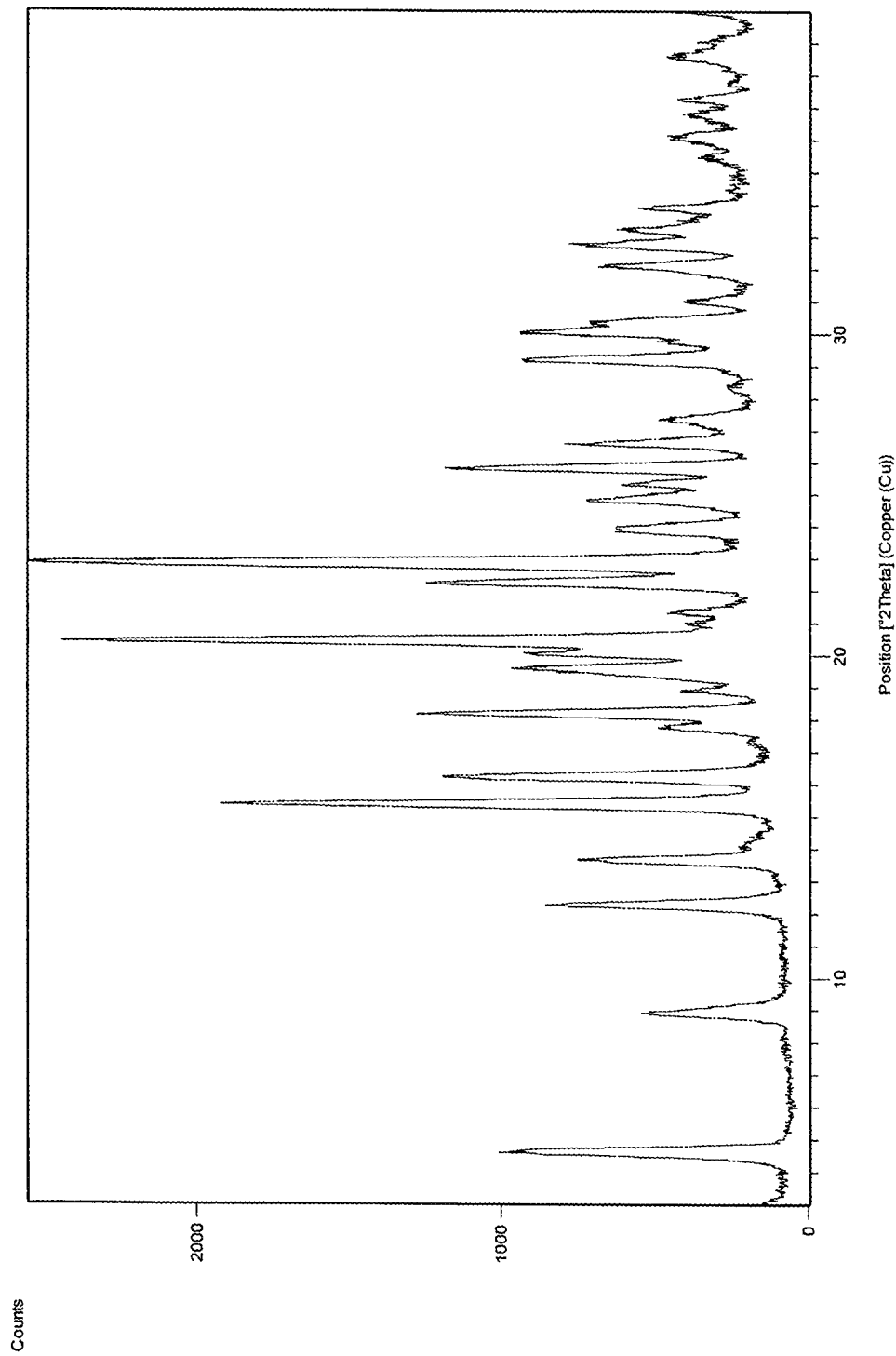
FIG. 1 depicts the X-Ray Powder Diffraction (XRPD) pattern of a dapagliflozin-citric acid co-crystal.
Figure 2:
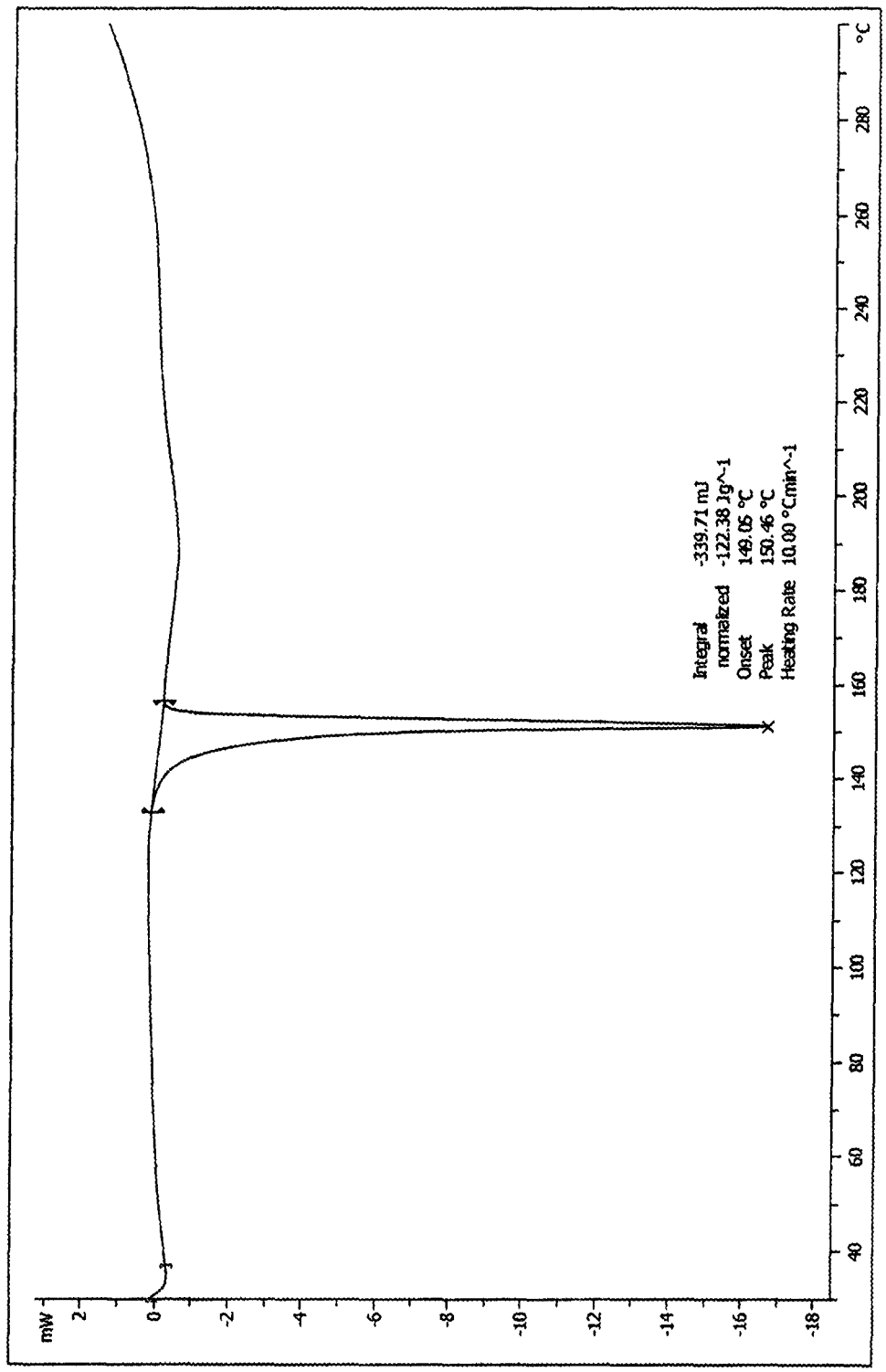
FIG. 2 depicts the Differential Scanning calorimetry (DSC) pattern of a dapagliflozin-citric acid co-crystal.

The term "about," as used herein, refers to any value which lies within the range defined by a number up to ±10% of the value.

The term "contacting," as used herein, refers to the act of bringing together two or more components by dissolving, mixing, suspending, blending, slurrying, or stirring.

The term "room temperature" as used herein refers to a temperature of about 20° C. to about 25° C.

The term "co-crystal," as used herein, refers to a stoichiometric multi component system comprising an active pharmaceutical ingredient (API) and a pharmaceutical co-crystal former wherein the active pharmaceutical ingredient and the pharmaceutical co-crystal former are connected by non-covalent interactions.

The term "co-crystal former," as used herein, refers to compounds which can form intermolecular interactions with an API and co-crystallize with it.

A first aspect of the present invention provides a dapagliflozin-citric acid co-crystal of Formula II.

Formula II

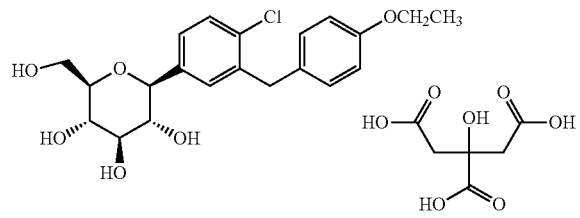

In one embodiment of this aspect, the dapagliflozin-citric acid co-crystal is characterized by X-ray powder diffraction peaks having d-spacing values at about 3.89, 3.90, 4.01, 4.35, 5.77, and 5.80 Å.

In another embodiment of this aspect, the dapagliflozin-citric acid co-crystal may further be characterized by X-ray powder diffraction peaks having d-spacing values (Å) at about 19.32, 18.85, 7.27, 7.21, 6.53, 5.80, 5.77, 5.74, 5.49, 5.46, 4.89, 4.53, 4.43, 4.35, 4.01, 3.90, 3.89, 3.71, 3.59, 3.52, 3.46, 3.36, 3.07, 2.98, 2.94, 2.89, 2.79, 2.74, and 2.70.

Table 1 provides the d-spacing values (Å) and their corresponding peak values (2θ) of a dapagliflozin-citric acid co-crystal.

TABLE 1

| Position (2θ) | d-spacing (Å) | Relative intensity |
|---|---|---|
| 4.57 | 19.32 | 33.46 |
| 4.68 | 18.85 | 35.48 |
| 8.85 | 9.89 | 17.23 |
| 12.18 | 7.27 | 24.15 |
| 12.27 | 7.21 | 31.84 |
| 13.57 | 6.53 | 22.71 |
| 15.27 | 5.80 | 49.59 |
| 15.36 | 5.77 | 73.26 |
| 15.45 | 5.74 | 61.93 |
| 16.13 | 5.49 | 35.65 |
| 16.24 | 5.46 | 46.61 |

TABLE 1-continued

| Position (2θ) | d-spacing (Å) | Relative intensity |
|---|---|---|
| 17.75 | 5.00 | 16.36 |
| 18.15 | 4.89 | 44.97 |
| 18.91 | 4.69 | 12.51 |
| 19.60 | 4.53 | 37.05 |
| 20.06 | 4.43 | 33.43 |
| 20.41 | 4.35 | 92.95 |
| 21.35 | 4.16 | 14.49 |
| 22.16 | 4.01 | 87.94 |
| 22.74 | 3.90 | 83.85 |
| 22.86 | 3.89 | 100 |
| 23.81 | 3.73 | 19.78 |
| 23.97 | 3.71 | 23.65 |
| 24.79 | 3.59 | 26.00 |
| 25.32 | 3.52 | 21.07 |
| 25.73 | 3.46 | 37.92 |
| 26.56 | 3.36 | 29.32 |
| 27.33 | 3.26 | 15.91 |
| 28.31 | 3.15 | 7.56 |
| 29.12 | 3.07 | 33.77 |
| 30.03 | 2.98 | 35.56 |
| 30.41 | 2.94 | 23.77 |
| 30.98 | 2.89 | 12.63 |
| 32.09 | 2.79 | 23.87 |
| 32.74 | 2.74 | 26.97 |
| 33.21 | 2.70 | 21.02 |
| 33.86 | 2.65 | 19.14 |
| 35.47 | 2.53 | 10.15 |
| 36.06 | 2.49 | 14.81 |
| 36.21 | 2.48 | 13.17 |
| 36.78 | 2.44 | 12.55 |
| 37.26 | 2.41 | 13.97 |
| 38.53 | 2.33 | 14.49 |
| 39.12 | 2.30 | 9.58 |

In another embodiment of this aspect, the dapagliflozin-citric acid co-crystal is characterized by a DSC thermogram having an endotherm at about 150° C.

Figure 3:
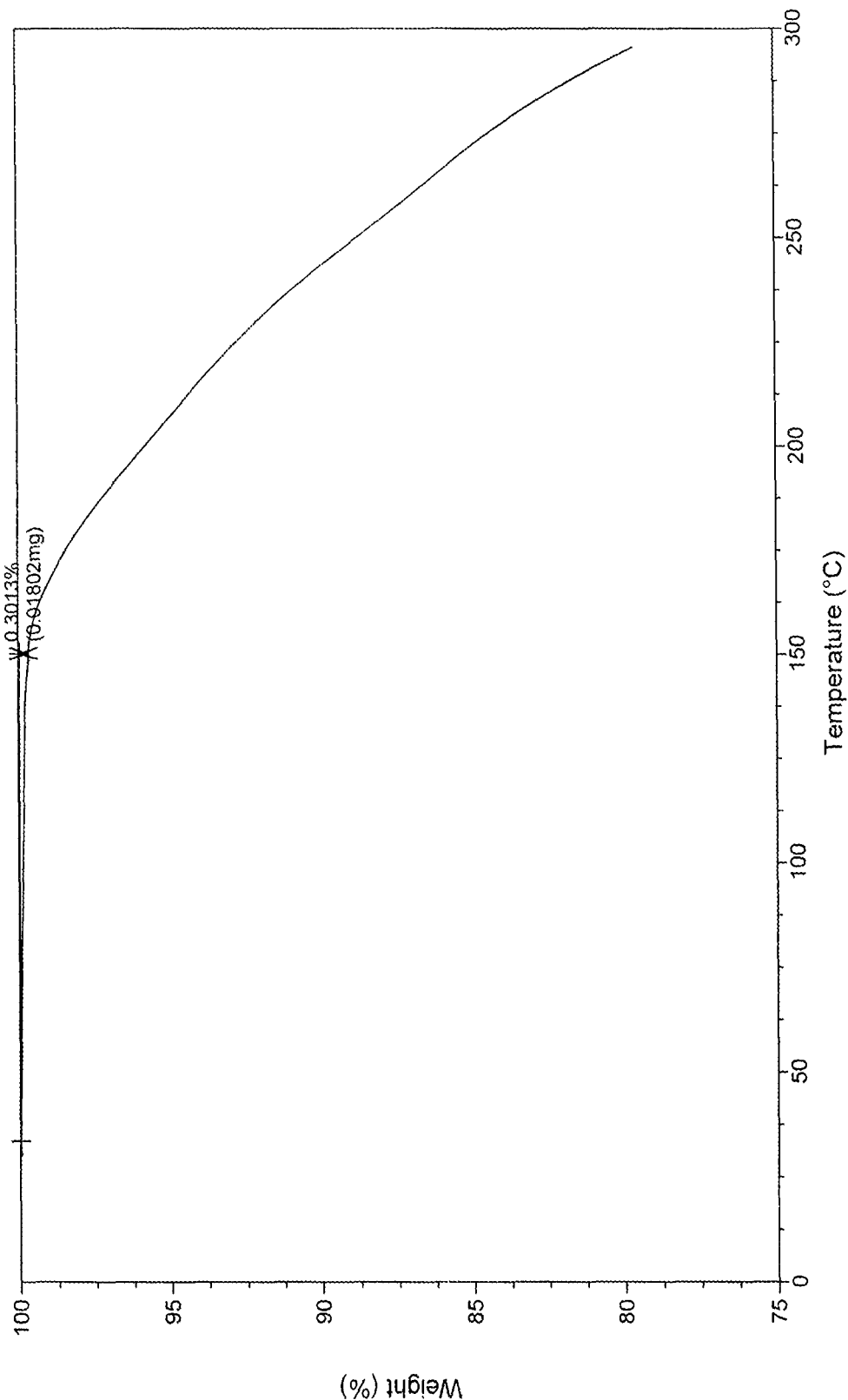
FIG. 3 depicts the Thermogravimetric Analysis (TGA) pattern of a dapagliflozin-citric acid co-crystal.

In another embodiment of this aspect, the dapagliflozin-citric acid co-crystal is characterized by a TGA thermogram substantially as depicted in FIG. 3.

In yet another embodiment of this aspect, the dapagliflozin-citric acid co-crystal is formed by the interaction of dapagliflozin and citric acid in a stoichiometric ratio of 1:1.

A second aspect of the present invention provides a process for the preparation of a dapagliflozin-citric acid co-crystal, comprising contacting dapagliflozin with citric acid in the presence of a solvent.

Dapagliflozin used as the starting material can be obtained by methods known in the art, for example, U.S. Pat. Nos. 6,515,117, 7,375,213, 7,932,379, and 7,919,598, which are incorporated herein by reference.

The solvent is selected from the group consisting of alcohols, ketones, carboxylic acids, chlorinated hydrocarbons, ethers, amides, polar aprotic solvents, alkyl acetates, and mixtures thereof.

Examples of alcohols include those primary, secondary, and tertiary alcohols having from one to six carbon atoms such as methanol, ethanol, 1-propanol, isopropanol, isobutanol, and butanol. Examples of ketones include acetone and methyl ethyl ketone. Examples of carboxylic acids include acetic acid and propionic acid. Examples of chlorinated hydrocarbons include dichloromethane, chloroform, and 1,2-dichloroethane. Examples of ethers include diethyl ether, methyl tertiary butyl ether, diisopropyl ether and tetrahydrofuran. Examples of polar aprotic solvents include N,N-dimethylformamide, N,N-dimethylacetamide, dimethylsulphoxide, acetonitrile, and N-methylpyrrolidone. Examples of alkyl acetates include methyl acetate, ethyl acetate, n-propyl acetate, isopropyl acetate, n-butyl acetate, and isobutyl acetate.

In a preferred embodiment, dapagliflozin is contacted with citric acid in an alkyl acetate, preferably ethyl acetate or isopropyl acetate.

A third aspect of the present invention provides a pharmaceutical composition comprising a dapagliflozin-citric acid co-crystal and one or more pharmaceutically acceptable carriers, diluents, or excipients.

A fourth aspect of the present invention provides the use of a dapagliflozin-citric acid co-crystal for the treatment of type 2 diabetes mellitus.

Methods:

The XRPD of the samples were determined by using a PANalytical®; Model X'Pert PRO; Detector: X'celerator®; Step size: 0.02; Scan Range: 3-40 degree 2 theta; CuKα radiation at 45 kV and 40 mA.

The DSC was recorded using a Mettler-Toledo® 821e. Data collection parameters: Scanning rate: 10° C./min; Temperature: 30° C. to 300° C.

The TGA of the samples were determined by using a TA Instruments® Q500 between 30° C. to 300° C. at 10° C./min scan rate.

The below examples are illustrated to aid the understanding of the invention but are not intended to and should not be construed to limit its scope in any way.

EXAMPLES

Example 1: Preparation of a Dapagliflozin-Citric Acid Co-Crystal

Dapagliflozin (0.25 g, 0.613 mmol) and anhydrous citric acid (0.117 g, 0.613 mmol) were added to isopropyl acetate (6 mL) at room temperature. The mixture was stirred for 30 minutes. Isopropyl acetate (8 mL) was added to the mixture, and then the mixture was stirred for one hour. Isopropyl acetate (10 mL) was added to the mixture and the resulting mixture was stirred for one hour. The material obtained was filtered, then washed with isopropyl acetate (5 mL), and then dried at room temperature under reduced pressure.

Yield: 0.237 g (64.5%)

$^1$H NMR (400 MHz, DMSO-D6): δ 1.31 (t, 3H, —CH$_2$CH$_3$), 2.65 and 2.75 (d, 2H, J=15.36 Hz, —CH$_2$ (citric acid)), 3.09-3.25 (m, 4H, H2, H3, H4, H5), 3.45 (m, 1H, H-6a), 3.69 (d, 1H, J=11.44 Hz, H-6b), 3.93-4.02 (m, 5H, H1, —CH$_2$, —CH$_2$), 4.44 (bs, 1H, —OH), 4.8 (bs, 1H, —OH), 4.95 (bs, 2H, —OH), 6.82 (d, 2H, J=8.56 Hz, Ar—H), 7.09 (d, 2H, J=8.56 Hz, Ar—H), 7.22 (d, 1H, J=8.24 Hz, Ar—H), 7.32 (s, 1H, Ar—H), 7.37 (d, 1H, J=8.24 Hz, Ar—H), 12.35 (bs, 3H, —COOH (citric acid))

Example 2: Preparation of a Dapagliflozin-Citric Acid Co-Crystal

Dapagliflozin (0.25 g, 0.613 mmol) and anhydrous citric acid (0.087 g, 0.455 mmol) were added to isopropyl acetate (6 mL). The mixture was stirred at room temperature for 30 minutes. Isopropyl acetate (8 mL) was added to the mixture, and then the mixture was stirred for one hour. Isopropyl acetate (10 mL) was added to the mixture, and then the mixture was stirred for one hour. The obtained material was filtered, then washed with isopropyl acetate (5 mL), and then dried at room temperature under reduced pressure.

Yield: 0.177 g (64.9%)

Example 3: Preparation of a Dapagliflozin-Citric Acid Co-Crystal

Dapagliflozin (0.25 g, 0.613 mmol) and anhydrous citric acid (0.175 g, 0.911 mmol) were added to isopropyl acetate (6 mL). The mixture was stirred at room temperature for 30 minutes. Isopropyl acetate (8 mL) was added to the mixture, and then the mixture was stirred for one hour. Isopropyl acetate (10 mL) was added to the mixture, and then the mixture was stirred for one hour. The material was filtered, then washed with isopropyl acetate (5 mL), and then dried at room temperature under reduced pressure.

Yield: 0.226 g (72.4%)

Example 4: Dapagliflozin-Citric Acid Co-Crystal

Dapagliflozin (0.25 g, 0.613 mmol) and anhydrous citric acid (0.117 g, 0.613 mmol) were added to ethyl acetate (0.5 mL). The mixture was stirred at room temperature for 30 minutes. Ethyl acetate (4 mL) was added to the mixture, and then the mixture was stirred for one hour. Ethyl acetate (4 mL) was added to the mixture, and then the mixture was stirred for seven hours. The material was filtered, then washed with ethyl acetate (5 mL), and then dried at room temperature under reduced pressure.

Yield: 0.238 g (64.77%)

Example 5: Dapagliflozin-Citric Acid Co-Crystal

Dapagliflozin (0.25 g, 0.613 mmol) and anhydrous citric acid (0.117 g, 0.613 mmol) were added to isobutyl acetate (0.5 mL). The mixture was stirred at room temperature for 30 minutes. Isobutyl acetate (4 mL) was added to the mixture, and then the mixture was stirred for one hour. Isobutyl acetate (10 mL) was added to the mixture, and then the mixture was stirred for seven hours. The material was filtered, then washed with isobutyl acetate (3 mL), and then dried at room temperature under reduced pressure.

Yield: 0.295 g (80.28%)

Example 6: Dapagliflozin-Citric Acid Co-Crystal

Dapagliflozin (0.25 g, 0.613 mmol) and anhydrous citric acid (0.117 g, 0.613 mmol) were added to tertiary butanol (0.5 mL). The mixture was stirred at room temperature for one hour. Diisopropyl ether (5 mL) was added to the mixture, and then the mixture was stirred for one hour. Tertiary butanol (2 mL) and diisopropyl ether (2 mL) were added to the mixture, and then the mixture was stirred for seven hours. The material was filtered, then washed with diisopropyl ether (2 mL), and then dried at room temperature under reduced pressure.

Yield: 0.1457 g (39.65%)

Example 7: Dapagliflozin-Citric Acid Co-Crystal

Dapagliflozin (0.25 g, 0.613 mmol) and anhydrous citric acid (0.117 g, 0.613 mmol) were added to methyl tertiary butyl ether (4 mL). The mixture was stirred at room temperature for 30 minutes. Methyl tertiary butyl ether (10 mL) was added to the mixture, and then the mixture was stirred for seven hours. The material was filtered, then washed with methyl tertiary butyl ether (3 mL), and then dried at room temperature under reduced pressure.

Yield: 0.302 g (82.19%)

We claim:

1. A dapagliflozin citric acid co-crystal.
2. The dapagliflozin citric acid co-crystal of claim 1, characterized by X-ray powder diffraction peaks having d-spacing values at about 3.89, 3.90, 4.01, 4.35, 5.77, and 5.80.
3. The dapagliflozin citric acid co-crystal of claim 1, characterized by a DSC having an endotherm at about 150° C.
4. The dapagliflozin citric acid co-crystal of claim 1, characterized by a TGA substantially as depicted in FIG. 3.
5. The dapagliflozin citric acid co-crystal of claim 1, wherein the dapagliflozin and citric acid are present in a stoichiometric ratio of 1:1.
6. A process for the preparation of a dapagliflozin citric acid co-crystal comprising contacting dapagliflozin with citric acid in the presence of a solvent.
7. The process of claim 6, wherein the solvent is selected from ethyl acetate, isopropyl acetate, isobutyl acetate, tertiary butanol, diisopropyl ether, or methyl tertiary butyl ether.
8. A pharmaceutical composition comprising a dapagliflozin citric acid co-crystal and one or more pharmaceutically acceptable carriers, diluents, or excipients.
9. A method of treating diabetes in a mammal comprising administering a therapeutically effective amount of the pharmaceutical composition of claim 8.

* * * * *